United States Patent [19]

Tryggvason et al.

[11] Patent Number: 4,677,058
[45] Date of Patent: Jun. 30, 1987

[54] DETECTING MALIGNANT CELLS WITH MONOCLONAL ANTIBODIES SPECIFIC TO TYPE IV COLLAGENASE ENZYME

[76] Inventors: Karl Tryggvason, Isterintie 10 B, 90230 Oulu 23, Finland; Lance A. Liotta, 5621 Sonoma Rd., Bethesda, Md. 20817

[21] Appl. No.: 496,230

[22] Filed: May 19, 1983

[51] Int. Cl.⁴ ........................................ G01N 33/577
[52] U.S. Cl. ........................................ 435/7; 424/3; 435/23; 435/29; 436/548; 436/813; 935/110
[58] Field of Search ............... 435/7, 23, 29; 436/533, 436/548, 813; 424/3; 935/110

[56] References Cited

U.S. PATENT DOCUMENTS

| | | | |
|---|---|---|---|
| 3,555,143 | 1/1971 | Axen | 436/533 |
| 3,985,620 | 10/1976 | Karges | 435/23 |
| 4,201,763 | 5/1980 | Monthony | 436/533 |
| 4,424,278 | 1/1984 | Bucovaz | 435/23 X |
| 4,443,367 | 4/1984 | Weingarten | 435/23 X |

OTHER PUBLICATIONS

Chemical Abstracts I, 89:55357q, (1978).
Chemical Abstracts II, 91:70720n, (1979).
Chemical Abstracts III, 93:43350b, (1980).
"Techniques in Immunocytochemistry", vol. 1, C. R. Bullock, ed., pp. 256–259, Academic Press, New York, 1982.
Liotta, L. A. et al., J. Nat'l Cancer Inst., 58 (5), 1427–1431, (1977).
Salo, T. et al., J. Biol. Chem., 258 (5), 3058–3063, (Mar. 1983).
Liotta, L. A. et al., Proc. Natl. Acad. Sci. U.S.A., 76 (5), 2268–2272, (1979).
Kohler, G. et al., Nature, 256, No. 5517, 495–497, (1975).

*Primary Examiner*—Sidney Marantz
*Attorney, Agent, or Firm*—Fay, Sharpe, Beall, Fagan, Minnich & McKee

[57] ABSTRACT

Basement membrane collagen degrading enzymes are provided which are useful for the detection of malignant cells with metastatic activity. Means for detecting such cells are also provided.

5 Claims, No Drawings

DETECTING MALIGNANT CELLS WITH MONOCLONAL ANTIBODIES SPECIFIC TO TYPE IV COLLAGENASE ENZYME

BACKGROUND OF THE INVENTION

The present invention relates to methods for the demonstration of metastatic cell activity by immunological determination of type IV collagenase antigen by use of polyclonal and monoclonal antibodies to said enzyme antigen. In addition, this invention discloses compositions, comprising labeled or unlabeled enzyme antigen and labeled or unlabeled polyclonal and monoclonal antibodies to said enzyme antigen.

DESCRIPTION OF THE PRIOR ART

One of the major characteristics of malignant cells is invasion and the formation of metastasis. Accordingly, methods for early detection and control of the invasive processes are of significant clinical value. The formation of metastasis is a complex sequence of events, whereby malignant cells detach from the primary tumor, invade the adjacent tissue, penetrate into the lymphatic or circulatory channels, attach to and penetrate the vessel wall at a distant site, invade the tissue and finally proliferate to initiate the metastatic focus.

The invading tumor cells have to penetrate basement membranes at several sites during the dissemination process. Basement membranes are extracellular matrices, which form a tough continuous sheet, which separates epithelial, endothelial and parenchymal cells from interstitial connective tissue. These structures are composed of collagen (type IV) and noncollagenous components such as laminin, proteoglycan and fibronectin. Basement membranes comprise significant barriers for the tumor cells and therefore their degradation is an important step in the process of metastasis. This process is now believed to be facilitated by proteolytic enzymes. Elevated levels of proteases such as plasminogen activators, cathepsin B and D and proteoglycan degrading enzymes have been described in both tumor tissue extracts and media of cultured tumor cells, and these enzymes have been considered as promising probes to measure the invasive potential of cells. However, the correlation between the release of the enzymes and invasiveness of malignant cells has not been established. In fact, plasminogen activators are produced by many cell lines with no invasive properties. Furthermore, since the above mentioned proteases do not degrade type IV collagen they do not provide sufficient means for tumor cells to traverse basement membranes.

The applicants have demonstrated that tumor cells release a neutral protease, which specifically degrades type IV collagen and have developed methods for the purification of this enzyme to homogeneity from a metastatic mouse tumor (Liotta et al., 7 Natl. Cancer Inst., 58, 1427-1431, 1977; Liotta et al., Proc. Natl. Acad. Sci., 76, 2268-2272, 1978; Salo et al., The Journal of Biological Chemistry, Vol. 258, pp. 3058-3063, 1983) and from cultured human tumor cells, as well. The applicants have also shown that the activity of this enzyme, herein referred to as type IV collagenase, correlates with the metastatic potential of tumor cells (Liotta et al., Nature 284, 67-68, 1980).

Since it has been demonstrated that the type IV collagenase enzyme antigen is useful for demonstrating malignant cells with metastatic nature, the enzyme can be of great diagnostic value. However, the measurement of the type IV collagenase activity cannot be accomplished in biological fluids, such as body fluids, tissue extracts or tissue sections due to the large amount of protease inhibitors in such samples.

SUMMARY OF THE INVENTION

It is the objective of the present invention to provide methods for detection of malignant tumor cells with metastatic cell activity by immunological determination of type IV collagenase enzyme antigen in biological samples, such as body fluids, tissue extracts, tissue sections, organ and cell cultures, culture medias, etc. A further objective of the present invention is to provide compositions, comprising both labeled and unlabeled highly purified type IV collagenase enzyme antigen and labeled or unlabeled polyclonal or monoclonal antibodies to said type IV collagenase enzyme antigen.

DETAILED DESCRIPTION OF THE INVENTION

Methods for purifying and characterizing the type IV collagenase antigen from cells capable of penetrating basement membranes, especially from malignant tumor cells, are an obligatory premise for the realization of the present invention. The applicants have discovered the type IV collagenase and developed methods for the purification and characterization of this antigen (Liotta et al., 7. Natl. Cancer Inst., 58, 1427-1431, 1977; Liotta et al., Proc. Natl. Acad. Sci., 76, 2268-2272, 1978; Salo et al., The Journal of Biological Chemistry, Vol. 258, pp. 3058-3063, 1983); Salo et al., 7. Biol. Chem., 1983). For the measurement of type IV collagenase activity, radioactively labeled type IV procollagen is used as a substrate, this substrate being prepared according to a method developed by the inventors (Tryggvason et al., Biochemistry, 19, 1284-1289, 1980). This actvity assay is required to determine the degree of purification during separate steps of the purification process. By this method the enzyme activity can be determined in serum-free organ or cell culture media.

The type IV collagenase enzyme can be obtained from serum-free organ culture media of malignant tumor tissue or media of cultured tumor cells. The tissue pieces or cells are usually cultured in vitro for 5 days and the media collected daily. The medium protein containing tye type IV collagenase antigen is precipitated with ammonium sulfate and then passed through several chromatography columns as described in the illustrative examples below.

The purified type IV collagenase antigen has a molecular weight of about 70,000 and when studied by gel electrophoresis, consists of two polypeptide chains having a molecular weight of 62,000 and 68,000. The type IV collagenase enzyme antigen needs proteolytic activation for maximal activity and has a pH optimum of 7.4. The type IV collagenase enzyme antigen is a metal dependent enzyme and needs calcium for activity. The enzyme antigen is specific and does not degrade interstitial collagen of types I, II or III, other basement membrane components or casein.

The isolation and purification of the type IV collagenase enzyme antigen makes it possible to produce specific antibodies to said enzyme antigen. The production of these antibodies enables the development of sensitive immunological methods to detect metastatic cell activity by the qualitative or quantitative determination of the type IV collagenase antigens in biological samples, such as body fluids, tissue extracts, tissue sections, cell or organ cultures, culture media, etc.

The preparation of antisera, polyclonal as well as monoclonal antibodies, can be carried out by already established methods. For the preparation of antisera the purified type IV collagenase antigen is injected several times subcutaneously into experimental animals, such as rabbits or guinea pigs and after a suitable period of time serum is withdrawn from the animal(s). The presence of the specific antibodies in the antiserum is then tested by techniques, such as the enzyme linked immunosorbent assay (ELISA), the western immunoblotting technique and immunological staining methods which are known to those skilled in the art.

Antisera have been produced to the murine type IV collagenase antigen by methods developed by the applicants. These antisera react with the mouse antigen as shown by immunoblotting, ELISA and immunofluorescence techniques.

For the preparation of conventional antiserum the type IV collagenase enzyme antigen has to be a highly pure and homogenous protein. It is extremely difficult to obtain sufficient amounts of absolutely pure human type IV collagenase antigen to produce conventional antisera in rabbits and guinea pigs. In order to overcome this problem, we have utilized the method of Köhler and Milstein (Nature, 256, 496, 1975) to prepare monoclonal antibodies. An advantage with this method is that the antigen need not be absolutely pure, because the specific antibody producing cell clones (hybrides) can be selected under in vitro conditions.

According to the method mentioned above, BALB/C mice were immunized twice subcutaneously with 100 µg of highly purified type IV collagenase isolated from culture media of human fibrosarcoma cells. After six weeks, the antisera were tested with the ELISA method. If the results received were satisfactory, the mice were immunized once more intravenously with a suitable amount of type IV collagenase antigen. Spleen cells from two immunized mice and mouse myeloma cells (NS-1) were then hybridized and cultured according to conventional technique in microtiter plates. Of 453 plated wells, 46 were positive for antibodies as determined by the ELISA method.

By the method described above, 10 suitable hybrid lines were found. These 10 hybrid lines were highly positive for malignant human fibrosarcoma and breast carcinoma cells but only weakly reactive with normal human skin fibroblasts. Three of those 10 hybrid cell lines, which had the highest titers were chosen for cloning in vitro by the dilution technique and for production of monoclonal antibodies.

The polyclonal and monoclonal antibodies to the type IV collagenase antigen produced, isolated and purified as described above, can be labeled with suitable radioactive, enzymatic or fluorescent labels by conventional methods, which should be apparent to those skilled in the art.

These said polyclonal and monoclonal antibodies and type IV collagenase antigen, labeled as well as unlabeled, could be bound to suitable solid carriers and used in the immunological methods, which form part of this invention.

According to the methods for detecting malignant cells with metastatic cell activity the presence of the type IV collagenase enzyme antigen is determined in biological samples, such as body fluids, tissue extracts and sections, etc. with conventional immunological methods by aid of labeled or unlabeled, bound or unbound type IV collagenase enzyme antigen compositions as well as labeled or unlabeled, bound or unbound, polyclonal or monoclonal antibody compositions.

In the immunological methods, rabbit antiserum was used to determine the presence of type IV collagenase antigen. As demonstrated by the western blotting technique, the antiserum stained two proteins in the 62 K and 68 K region, which correspond to the purified type IV collagenase enzyme antigen. Furthermore, the antiserum was used for immunological staining of human breast cancer and normal breast tissues. Cryosections of the tissues were first incubated with the antiserum and then with FITC-conjugated anti-rabbit IgG. The results showed that of 10 normal tissue samples, no one gave a positive fluorescence, i.e., they did not contain the type IV collagenase antigen. On the other hand, 25 out of 25 breast cancer tissue samples showed intense fluorescence in the border region of the tumor. Accordingly, the immunological methods described in this invention can detect the presence of malignant tumor cells in tissues, and since the staining was seen primarily at the border of the tumor, it is evident that the type IV collagenase antigen is enriched in invasive cells.

Antibodies to human type IV collagenase enzyme antigen produced from mouse hybrid clones were used for immunological staining of cultured cells. The cells studied were human fibrosarcoma (HT-1080), breast carcinoma cells (MCF-7) and normal human skin fibroblasts. The cells were cultured on microtiter plates and incubated with the antibodies. The plates were then washed and incubated with biotinylated horse antimouse IgG/IgM and washed. After that, avidinbiotin-peroxidase reagents were added to color the mouse immunoglobulin-antimouse immunoglobulin complexes bound to the cells. The results showed that the malignant HT-1080 and MCF-7 cells were stained, whereas the normal skin fibroblasts were not stained. Thus it is apparent that monoclonal antibodies to human type IV collagenase can be used to differentiate malignant cells containing the type IV collagenase enzyme antigen from normal cells not containing said enzyme antigen.

The invention is disclosed in further detail in the illustrative examples below.

EXAMPLE 1

Isolation of type IV collagenase antigen

For the preparation of mouse type IV collagenase metastatic PMT tumors are first grown in C57131/6J mice. After about two weeks of growth, the tumors are excised, minced and incubated in a serum-free RPMI-1640 medium as organ cultures for 5 days. The medium is collected daily and its protein precipitated with ammonium sulfate (25–60% saturation). The precipitate is dissolved in the enzyme buffer (0.05M Tris-HCl, pH 7.4, 0.2 M NaCl, 10 mM $CaCl_2$) and passed through a concanavalin-A agarose column to which most of the enzyme activity becomes bound. The bound activity is eluted with 1 M α-methyl mannoside and passed over a type IV collagen agarose column. The collagen coupled to the column is extracted from the EHS basement membrane matrix forming tumor and purified, and it contains intact type IV collagen chains (185 K and 175 K). In order to avoid degradation of the collagen-agarose by the enzyme, the buffers are devoid of $CaCl_2$ during that column run. The enzyme activity is eluted from the column with enzyme buffer containing 1M NaCl. The final purification of the enzyme is obtained by molecular sieve, e.g., Bio-Gel A 0.5 m, where it migrates with an apparent molecular weight of about 160,000. The enzyme purified in this way contains two polypeptide chains of molecular weights 68 K and 62 K.

The human type IV collagenase enzyme is prepared in the same way as the murine enzyme from serum-free media of cultured human fibrosarcoma cells (HT-1080). The cells are cultured in Dulbeccos modified Eagle's medium (DMEM) containing 10% fetal confluency in calf serum in roller bottles after which the medium is changed to the same serum-free medium. The medium is collected daily for 5 days.

EXAMPLE 2

Preparation of antiserum to mouse type IV collagenase

The antigen (100–200 µg) is injected subcutaneously in equal volumes of phosphate buffered saline (PBS) and Freund's complete adjuvant and again after 4 weeks with incomplete Freund's adjuvant. Booster injections are then given twice with 3 week intervals. Blood is drawn 3 weeks after the last booster an the serum tested for specificity and titer by ELISA, western blotting and immunostaining techniques.

EXAMPLE 3

Preparation and characterization of monoclonal antibodies

BALB/C mice are immunized with 100 µg of partially purified HT-1080 enzyme in complete Freund's adjuvance, and reimmunized twice with 50 µg of antigen, with 3 week intervals. The titers of antisera are tested 3 weeks after the last injection and being satisfactory (dilution $\leq$ 1:500) as determined by ELISA the animals are given 50 µg of antigen intravenously. Four days later the hybridization is carried out according to Köhler & Milstein (Nature, 256, 496, 1975). Immunized spleen cells from two mice are fused with NS-1 or corresponding myeloma cells and the fused cells are plated on 96-well microtiter plates at about $2 \times 10^5$ cells/well and mouse peritoneum cells (macrophages) are used as feeder cells ($6 \times 10^3$). The cells are cultured in a selective HAT-medium (DMEM containing $10^{-4}$M hypoxanthine, $10^{-7}$M aminopeptine, $1.6 \times 10^5$M and 20% FCS) for 3–4 weeks. This medium allows only the hybrid cells to grow. The cells are tested for antibody production with ELISA and usually about 10% of the wells are positive. The specificity of the antibodies is also tested by the western blotting technique and immunological staining.

The ELISA-method is carried out using 96-well microtiter plates. About 50–100 ng of antigen is put into each well and dried. Free binding sites are blocked by incubation for 30 min with 50 µl of 1% FCS and the wells are washed with PBS. Hybrid supernates as antisera are then added to the wells (50 µl) and incubated. After washing with PBS 50 µl of biotinylated horse anti-mouse IgG solution containing 1% FCS is added and incubated for 30 min followed by a wash with PBS. After that, an avidin-biotin-peroxidase reagent is added and incubated. After that, the perioxidase substrate (0.01% o-dianisidine, 0.01% $H_{2o2}$ in PBS) is added and the brown color formed is measured in a Titertek Multiscan spectrophotometer.

The western blotting technique can be used to better characterize the antibodies because it shows to exactly which polypeptide chains the antibody reacts with. The antigen or a protein mixture containing the antigen is first separated on a 10% sodium dodecyl sulfate polyacrylamide gel electrophoresis after which the proteins are blotted horizontally to a nitrocellulose sheet using 0.1 A current overnight. The sheet is then stained with a heparin-toluidine staining solution. The protein containing nitrocellulose strips are then cut out and the color removed with a solution (50% ethanol, 8% acetic acid, 42% water). The immunostaining of the strips is then carried out with the same method as used in the ELISA. Positive antibodies give a brown color of the antigen only, but it has to be noticed that if the antibody is directed against tertiary structure of the antigen one can get a negative result because the proteins are denatured during the gel electrophoresis.

EXAMPLE 4

Immunostaining of type IV collagenase

Rabbit antiserum to purified mouse type IV collagenase was used to study the localization of the enzyme in normal breast and malignant breast cancer human tissues. Cryosections (5 µm thick) from 10 normal breast tissue samples and 25 breast cancer tissue samples were preincubated with 1% FCS and then washed with PBS. After that the antiserum, 1:50 dilution, was incubated with the samples for 2 h at 20° C. followed by washing with PBS. The sections were then incubated with FITC-conjugated goat anti-rabbit serum overnight at 4° C. and washed with PBS. The fluorescence was then studied. The results showed that none of the normal tissues became stained whereas all of the 25 cancer tissues gave a clear fluorescence. The staining was most intense in the edge front of invasive tumors and between 10–80% of the tumor cells were positive.

Monoclonal antibodies against human HT-1080 sarcoma cell type IV collagenase were used to stain cultured HT-1080 cells, human breast carcinona cells (MCF-7) and human skin fibroblasts. The cells were cultured on cover slips to subconfluency and fixed with methanol at $-20°$ C. for 10 min. The cells were then preincubated with 1% FCS and washed with PBS after which they were incubated with the mouse antibodies for 2 hrs. at 20° C. and washed. Then, the cells were incubated for 30 min. with biotinylated horse anti-mouse IgG, washed and incubated with an avidin-biotin-peroxidase reagent. Finally, the cells were incubated with the peroxidase substrate. The antibodies gave a clear staining of the malignant HT-1080 and MCF-7 cells whereas the fibroblasts were negative.

Both examples of immunostaining indicate that the antibodies to type IV collagenase can detect malignant tumor cells with invasive properties.

While the present invention has been described by reference to certain illustrative examples, various modifications and variants within the spirit and the scope of the invention will be apparent to those skilled in the art.

What we claim is:

1. A method of detecting malignant cells with metastatic cell activity comprising:
  a. preparing monoclonal antibodies that bind specifically to type IV collagenase enzyme antigen;
  b. adding said monoclonal antibodies to a biological sample of the subject to be tested; and
  c. measuring the antigen-monoclonal antibody reaction in said biological sample.

2. The method of claim 1, wherein the monoclonal antibodies that bind specifically to type IV collagenase enzyme antigens are labelled.

3. The method of claim 1, wherein the monoclonal antibodies that bind specifically to type IV collagenase enzyme antigens are coupled to solid carriers.

4. A method of detecting malignant cells with metastatic cell activity comprising:
   a. preparing monoclonal antibodies that bind specifically to type IV collagenase enzyme antigen;
   b. preparing second antibodies to said monoclonal antibodies;
   c. labelling said second antibodies;
   d. adding the monoclonal antibodies to a biological sample of the subject to be tested;
   e. incubating the biological samples containing the monoclonal antibodies;
   f. adding the second labelled antibodies to the biological sample containing the monoclonal antibodies; and
   g. measuring the antigen-monoclonal antibody-second labelled antibody reaction in said biological sample.

5. A method of detecting malignant cells with metastatic cell activity comprising:
   a. preparing monoclonal antibodies that bind specifically to type IV collagenase enzyme antigen;
   b. labelling type IV collagenase enzyme antigens;
   c. adding said monoclonal antibodies and said labelled type IV collagenase enzyme antigens to biological samples of the subject to te tested;
   d. incubating the resultant mixture; and
   e. measuring the antigen-monoclonal antibody and the labelled antigen-monoclonal antibody reactions in said biological sample.

* * * * *